United States Patent [19]

Ong

[11] Patent Number: 5,042,893
[45] Date of Patent: Aug. 27, 1991

[54] DIRECT MOUNT COUPLING TO A SPECTROPHOTOMETER

[75] Inventor: Ronald G. J. Ong, Menlo Park, Calif.

[73] Assignee: Hewlett-Packard Company, Palo Alto, Calif.

[21] Appl. No.: 611,238

[22] Filed: Nov. 9, 1990

[51] Int. Cl.$^5$ .............................................. G02B 6/26
[52] U.S. Cl. .................................. 385/49; 356/326; 356/328; 385/31; 385/121
[58] Field of Search ............... 350/96.10, 96.11, 96.12, 350/96.13, 96.14, 96.15, 96.17, 96.18, 96.19; 356/326, 328

[56] References Cited

U.S. PATENT DOCUMENTS

| | | | |
|---|---|---|---|
| 4,337,993 | 7/1982 | Kompfner | 350/96.19 |
| 4,453,802 | 6/1984 | Bridges et al. | 350/96.14 X |
| 5,018,813 | 5/1991 | Rooby et al. | 350/96.14 |

Primary Examiner—John D. Lee
Assistant Examiner—Phan T. Heartney

[57] ABSTRACT

A fiber optic coupler for use with a diode array spectrophotometer system that optimizes the optical interface between a first fiber optic waveguide employed to couple light from a sample under analysis and a diode array spectrograph. The coupler comprises a fiber optic waveguide connector that secures the first optical fiber waveguide that couples light from the sample under investigation. A slit block is provided that has a relatively thin, rectangular exit aperture having dimensions compatible with the spectrograph. A single waveguide (or plurality of fiber optic waveguides) is coupled between the connector and the exit aperture and is arranged to have a generally round cross section adjacent the connector and a linear cross section adjacent the spectrograph. Improved light throughput is achieved at the fiber optic waveguide-spectrophotometer interface, when compared with conventional fiber optic spectrophotometer designs. The coupler provides for easier assembly at the fiber optic waveguide to spectrophotometer interface and minimizes the total number of optical components in the system. The present invention eliminates misalignment of the fiber-slit interface of conventional designs, and provides better sensitivity and signal to noise. Furthermore, the present invention is simpler, and reduces the total number of optically active components which results in a lower unit cost. The use of fixed parts in the coupler eliminates light loss associated with the tedius and difficult manual alignment at the fiber-slit interface. As a consequence, better sensitivity is achieved.

20 Claims, 2 Drawing Sheets

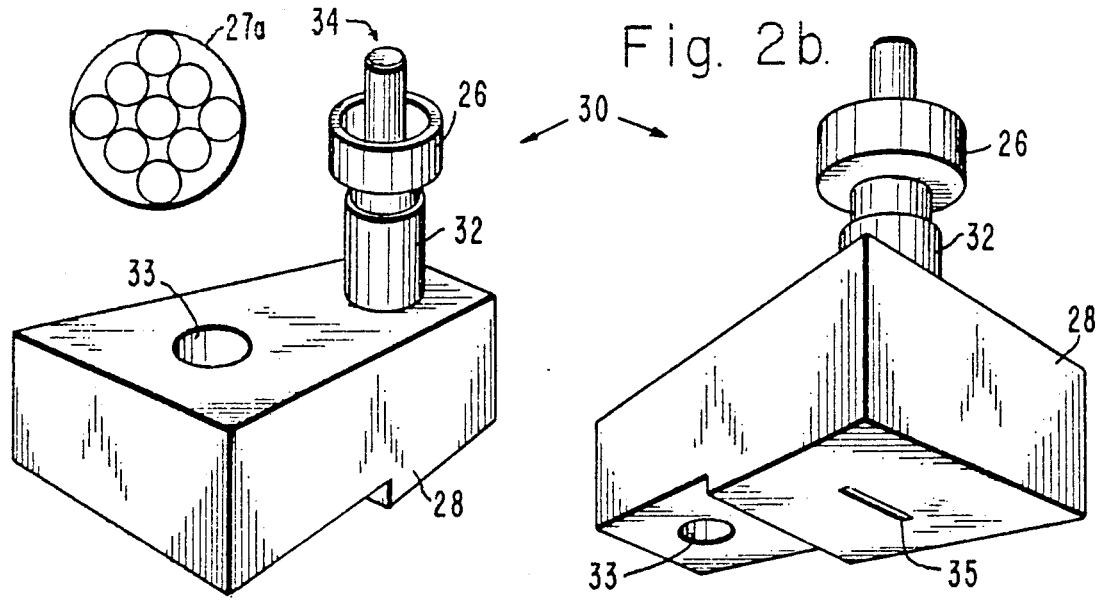
Fig. 2b.
Fig. 2a.
Fig. 3a.
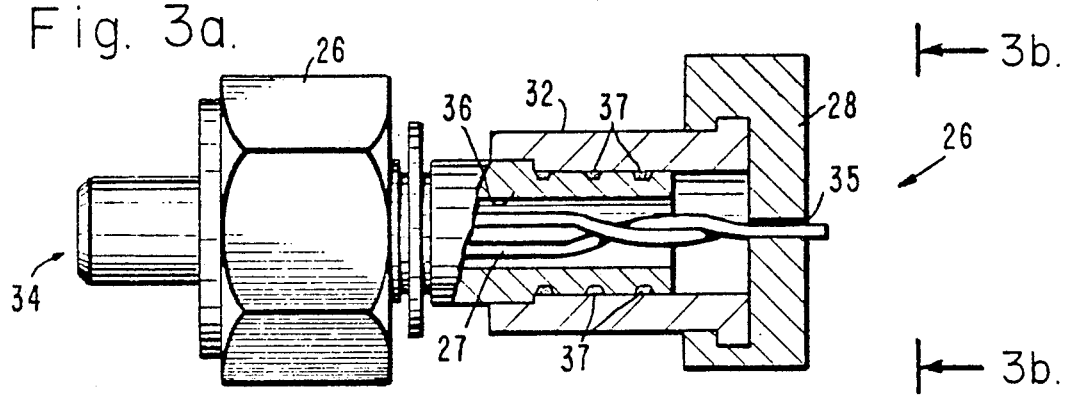
Fig. 3b.
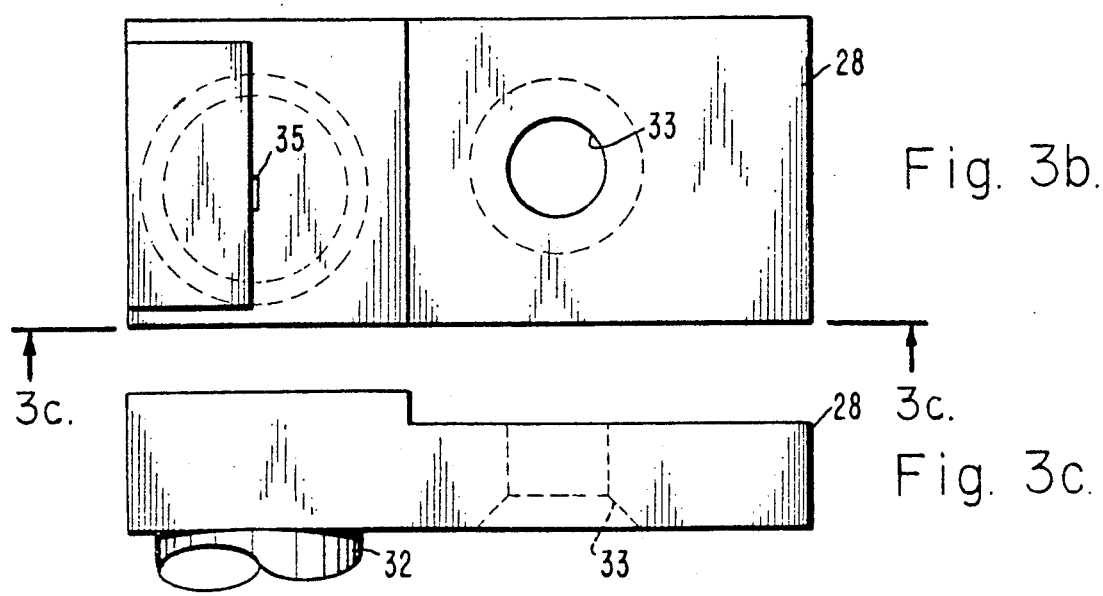
Fig. 3c.

3,042,893

DIRECT MOUNT COUPLING TO A SPECTROPHOTOMETER

BACKGROUND

The present invention relates generally to diode array spectrophotometers, and more particularly, to a direct mount fiber optic array coupler for use with a diode array spectrophotometer.

Diode array spectrophotometer designs typically employ a sealed spectrophotometer unit comprising a polychromator that includes an entrance slit, a holographic grating, and a diode array detector. Diode array spectrophotometers are considered to have "reversed optics", in that all wavelengths of light excite the sample, and are usually considered to be nonconventional relative to a forward optics spectrophotometer wherein filtered monochromatic light is employed.

Polychromatic light from a light source is passed through a sample under investigation and is coupled to the spectrophotometer unit by way of a focusing lens arrangement that focuses light onto the entrance slit of the spectrograph. The standard configuration of a Hewlett-Packard spectrophotometer model HP 8452A includes a lens to focus light onto the entrance slit. This arrangement works very well for non-remote applications. When using fiber optics for remote sampling, the goal is to minimize the light loss by optimizing the fiber-spectrograph interface. Conventionally this is done by butt-coupling the fiber onto the slit and is characterized by a significant reduction in light throughput.

With conventional fiber optic designs, light from the source is inefficiently coupled into the spectrophotometer unit. Light loss occurs at the interface between the fiber optic waveguide bundle and the entrance slit. Light losses of as much as 90% can occur in such conventional systems.

Accordingly, it is an objective of the present invention to provide for an improved fiber optic coupling for use with a diode array spectrophotometer. It is a further objective of the present invention to provide for a fiber optic coupling that limits light loss at the diode array spectrophotometer entrance.

SUMMARY OF THE INVENTION

In accordance with these and other objectives and advantages of the present invention, there is provided a new and improved fiber optic coupler for use with a diode array spectrophotometer that optimizes the optical interface between a fiber optic waveguide employed to couple light from a sample under analysis to the diode array spectrophotometer entrance aperture. The present invention replaces the conventional slit with a slit block that interfaces to a linear array fiber optic bundle whose output emulates the slit. The diode array spectrophotometer includes a spectrograph comprising an entrance aperture, a holographic grating and a photodiode array. The single core optical fiber waveguide is adapted to couple light from a sample under investigation to the general location of the spectrograph. The coupler comprises a fiber optic waveguide connector adapted to secure the single core optical fiber waveguide at its input end. A sleeve engages the periphery of an output end of the connector. The slit block is secured to the sleeve and has a relatively thin, rectangular exit aperture that has dimensions substantially the same as the entrance slit that is replaced in the spectrograph.

A plurality of fiber optic waveguides are coupled between the fiber optic waveguide connector and the slit block exit aperture that are arranged to have a generally round cross section at their respective first ends adjacent the connector. The plurality of waveguides have their first ends disposed in the fiber optic waveguide connector adjacent the single core fiber optic waveguide, and have their respective second ends disposed in the exit aperture of the slit block. The second ends of the plurality of waveguides are disposed in a generally linear arrangement along the length of the exit aperture and hence are arranged as a linear waveguide array at the exit aperture. The fiber optic coupler arrangement provides for an aspect ratio transformation of the plurality of fiber optic waveguides from a round input cross section to a linear output cross section that corresponds to the dimensions of the entrance slit that is replaced in the spectrograph.

In the present form of the coupler of the present invention, a linear array of single core fibers forms the image of the existing entrance slit of the spectrophotometer. However, one could use a single core fiber that has a rectangular end that exactly matches the cross section of the entrance slit. In this case, the performance is enhanced.

The coupler of the present invention eliminates the need for a separate physical entrance slit plate and enables all the light exiting from the plurality of fiber optic waveguides to be used by the spectrophotometer. The physical characteristics and dimensions of the fiber array are chosen to be substantially the same as the spectrophotometer entrance slit that it replaces.

The coupler of the present invention provides for easier assembly at the fiber optic waveguide to spectrophotometer interface and minimizes the total number of optical components in the system. By employing the present invention, improved light throughput is achieved at the fiber optic waveguide to spectrophotometer interface, when compared with conventional fiber optic spectrophotometer designs. The present invention eliminates misalignment of the fiber-slit interface of conventional designs, and provides better sensitivity and signal to noise. Furthermore, the present invention is simpler, and reduces the total number of optically active components which results in a lower unit cost. The use of fixed parts in the present invention eliminates the light loss associated with the tedious and difficult manual alignment at the fiber-slit interface. As a consequence, better sensitivity is achieved.

BRIEF DESCRIPTION OF THE DRAWINGS

The various features and advantages of the present invention may be more readily understood with reference to the following detailed description taken in conjunction with the accompanying drawings, wherein like reference numerals designate like structural elements, and in which:

FIGS. 2a and 2b are diagrams showing perspective views of the fiber optic coupler of the present invention; and FIGS. 3a, 3b and 3c show several views of the fiber optic coupler of FIG. 2.

DETAILED DESCRIPTION

Figure 1:
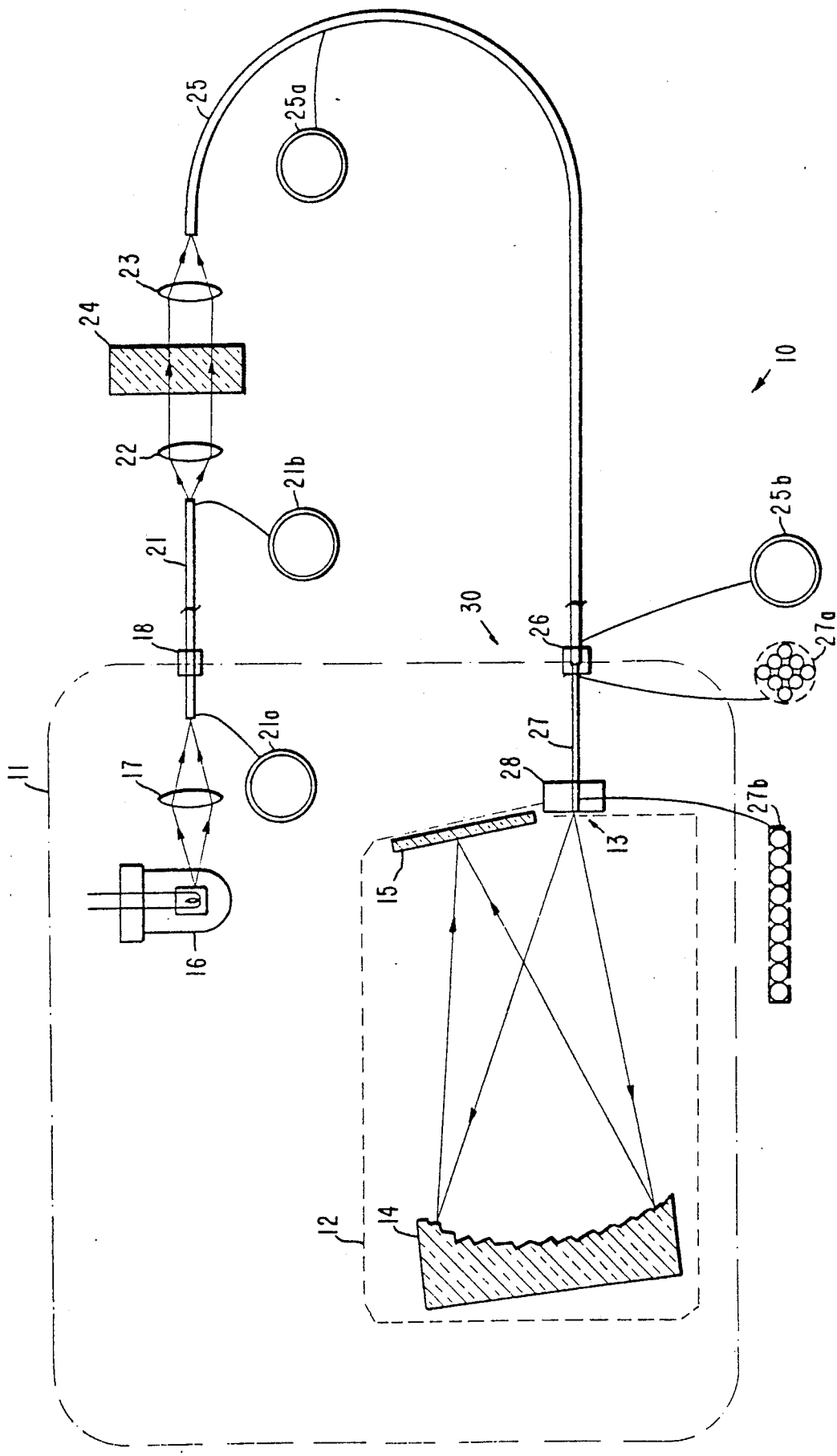
FIG. 1 is an illustration of a spectrophotometer incorporating a fiber optic coupler in accordance with the principles of the present invention.

Referring to FIG. 1, it shows a spectrophotometer system 10 incorporating a fiber optic coupler 30 in accordance with the principles of the present invention. The spectrophotometer system 10 comprises a spectrophotometer unit 11 that includes a spectrograph 12 comprising an entrance aperture 13, a holographic grating 14 and a photodiode array detector 15. The spectrophotometer unit 11 also includes a lamp source 16 that emits polychromatic light in the ultraviolet, visible and infrared spectral regions, a focusing lens 17, and an SMA connector 18 adapted to secure a first single core fiber optic waveguide 21 therein. The focusing lens 17 is adapted to focus light emitted by the lamp source 16 onto an input end of the first single core fiber optic waveguide 21. The cross section of the first single core fiber optic waveguide 21 is round, as is illustrated by the cross sectional symbols 21a, 21b shown adjacent thereto.

First and second collimating lenses 22,23 are located adjacent an output end of the first single core fiber optic waveguide 21 in the vicinity of a sample testing area. It is to be understood that multicore fibers may also be used as the waveguide 21. It is to be further understood that numerous sampling arrangements may be readily employed in addition to the multiple lens arrangement disclosed herein, as is well-known in the art. The sampling arrangement is typically determined by the specific application. Light coupled by the first single core fiber optic waveguide 21 is collimated by the collimating lenses 22,23 and the collimated light is passed through a sample 24 under investigation. A second single core fiber optic waveguide 25 has an input end adapted to receive light transmitted by the second collimating lens 23 and transmit the light to the spectrophotometer unit 11. The cross section of the second single core fiber optic waveguide 25 is also round, as is illustrated by the cross sectional symbols 25a, 25b shown adjacent thereto.

The fiber optic coupler 30 of the present invention is employed to interface between the second single core fiber optic waveguide 25 and the spectrograph 12. The fiber optic coupler 30 comprises a modified SMA connector 26, a slit block 28, and a fiber optic waveguide bundle 27 comprising a plurality of individual fiber optic waveguides. The cross section of the waveguide bundle 27 adjacent the modified SMA connector 26 is illustrated by the cross sectional symbol 27a shown adjacent thereto. The cross section of the waveguide bundle 27 adjacent the slit block 28 is illustrated by the cross sectional symbol 27b shown adjacent thereto.

With reference to FIG. 2, FIGS. 2a and 2b are diagrams showing perspective views of the fiber optic coupler 30 of the present invention. FIG. 2a shows a top perspective view of the coupler 30 showing the modified SMA connector 26 which comprises an input end 34 and a sleeve 32 that is adapted to secure the modified SMA connector 26 to the slit block 28. A through hole 33 is shown that is adapted to secure the slit block 28 to the spectrograph 12. The cross section of the waveguide bundle 27 adjacent the modified SMA connector 26 is illustrated by the cross sectional symbol 27a shown adjacent thereto. FIG. 2b shows a bottom perspective view of the coupler 30 showing the modified SMA connector 26, the sleeve 32, the slit block 28 and the through hole 33. In addition, an exit aperture 35 of the slit block is shown along with the cross section of the waveguide bundle 27 adjacent the slit block 28, illustrated by the cross sectional symbol 27b shown adjacent thereto.

With reference to FIG. 3, FIGS. 3a,3b and 3c show several views of portions of the fiber optic coupler 30 of FIG. 2. With reference to FIG. 3a, a partial cutaway view of the modified SMA connector 26 is shown. The modified SMA connector 26 comprises the input end 34 that is adapted to secure the second single core fiber optic waveguide 25 therein, and an output end 36 that extends toward the slit block 28. The sleeve 32 extends around the output end 36 of the modified SMA connector 26 and is secured by means of epoxy, for example, assisted by a plurality of grooves 37 milled in the periphery of the output end of the modified SMA connector 26, and the sleeve 32 is also secured to the slit block 28 in a conventional manner. The slit block 28 has its exit aperture 35 adapted to secure the plurality of individual fiber optic waveguides of the fiber optic waveguide bundle 27, assisted by means of epoxy, for example. The transition of the cross section of the plurality of individual fiber optic waveguides is illustrated in the exposed center of the output end 36 of the modified SMA connector 26.

FIG. 3b shows an end view of the coupler 30 taken in the direction of the arrows 3b in FIG. 3a. This view shows the bottom of the slit block 28 and shows the relative positions of the through hole 33, the exit aperture 35 and the mounting arrangement provided to secure the sleeve 32 in the slit block 28. FIG. 3c shows a side view taken in the direction of the arrows 3c in FIG. 3b. This view shows the slit block 28, the through hole 33 and the interface of the sleeve 32 to the slit block 28.

In operation, the coupler 30 is adapted to couple light from the second single core fiber optic waveguide 25 into the spectrograph 12. It does this in a highly efficient manner by using the plurality of smaller diameter waveguides comprising the fiber optic waveguide bundle 27 that interfaces to the second single core fiber optic waveguide 25 and transforms the optical information transmitted thereby into a line source compatible with the photodiode array detector 15 of the spectrograph 12.

The coupler 30 of the present invention eliminates the need for a separate physical entrance slit plate of the spectrograph 12 and enables all the light exiting the waveguide bundle 27 to be used by the spectrograph 12. The physical characteristics and dimensions of the waveguide bundle 27 are chosen to match the characteristics and dimensions of the spectrophotometer entrance slit. The fiber waveguide bundle 27 performs an aspect ratio transformation from a round input to a slit output. In order to interface to an HP 8452A spectrophotometer, for example, a bundle of nine 0.12 NA 50/55 $\mu$m all-silica fibers, for example, may be used to produce a fiber array slit with dimensions of approximately 50 $\times$ 500 $\mu$m.

In a conventional reversed optics type diode array spectrophotometer, the spectrograph is a sealed unit that comprises a polychromator (entrance slit and holographic grating) and a diode array detector. Polychromatic light from a light source is passed through the sample area and focused on the entrance slit of the polychromator. The polychromator disperses the light onto the diode array, and each diode is dedicated to measuring a narrow band of the spectrum. This optical system requires careful alignment and attachment of the grating inside the spectrograph. Subsequently, the spectrograph grating is aligned to the optical slit to optimize the polychromator dispersion of light onto the diode array detector 15.

In the spectrophotometer system 10 employing the coupler 30 of the present invention, polychromatic light from the lamp source 16 is passed through the sample area 24 and focused into the second single core fiber optic waveguide 25. The second single core fiber optic waveguide 25 carries the light to the coupler 30 by way of the modified SMA connector 26. The light exiting from the coupler 30 and into the spectrograph 12 is used in the same way as the light exiting the optical slit plate in a conventional spectrograph.

The features of the coupler 30 of the present invention include the following. Elimination of alignment-related problems of the optical fiber waveguide bundle 27 with an entrance slit plate of a conventional spectrograph. Rather, alignment of the grating 14 and diode array detector 15 of the spectrograph 12 are calibrated against the fiber optic linear array much as they would have been against the optical entrance slit plate which is replaced. The coupler 30 may be mounted without significantly altering the regular spectrograph assembly process, and without requiring different alignment machinery.

As compared to current alternative fiber optic spectrophotometry configurations, this direct coupling method significantly improves the light throughput of the overall system at the fiber optic waveguide - spectrophotometer interface. For any given light intensity entering the fiber optic system at the sample area, the major source of light loss in the direct coupling approach occurs at the modified SMA connector 26 interface. On the basis of simple active transmission area overlap calculations, one might expect about 50% light loss at this connection when coupling a 200 $\mu$m single core fiber to a bundle of 50/55 $\mu$m fibers. Since there are no optical impediments at the array slit end, there are no losses associated with the actual fiber optic-spectrograph interface.

In contrast, alternative configurations have their major source of light loss, in addition to those in the sample area, occurring at the fiber optic waveguide-spectrograph interface. For example, in the case of butt-coupling a 600 $\mu$m single core light-carrying fiber over a conventional entrance slit with dimensions of approximately 50 $\times$ 500 $\mu$m, similar area overlap analysis predicts light losses of almost 90% at the fiber optic waveguide-spectrograph interface.

Actual comparisons between a standard Hewlett-Packard spectrophotometer model HP 8452A, a Hewlett-Packard spectrophotometer model HP 8452A with a single core fiber mounted over the entrance slit, and a modified Hewlett-Packard spectrophotometer model HP 8452A with the coupler 30 of the present invention were made. These measurements were taken using a direct light source-to-spectrograph transmission path. It was found that the spectrometer employing the coupler 30 of the present invention outperforms the alternative fiber optic waveguide to spectrophotometer configurations.

The coupler 30 is relatively simple, and there are no moving parts. No complicated alignment mechanisms are required to ensure high optical throughput, and hence, there is no trade-off between coupling efficiency and larger alignment tolerances. The coupler 30 has a lower unit cost, provides better performance, and provides for better reproducibility of data than the optical coupling arrangements of conventional designs.

Thus there has been described a new and improved fiber optic coupler for use with a diode array spectrophotometer. It is to be understood that the above-described embodiment is merely illustrative of some of the many specific embodiments which represent applications of the principles of the present invention. Clearly, numerous and other arrangements can be readily devised by those skilled in the art without departing from the scope of the invention.

What is claimed is:

1. A fiber optic coupler for use with a diode array spectrophotometer that comprises a diode array spectrograph including a holographic grating and a photodiode array, and a first optical fiber waveguide adapted to couple light from a sample under investigation to the spectrograph, said coupler comprising:

means for receiving an optical fiber waveguide;

a slit block having a relatively thin, rectangular exit aperture that has predetermined dimensions compatible with the diode array spectrograph; and a second optical fiber waveguide coupled between the means for receiving an optical fiber waveguide and the slit block adjacent its exit aperture, the second optical fiber waveguide having a generally round cross section at an end adjacent the means for receiving an optical fiber waveguide, and having a generally linear cross section proximal to the exit aperture of the slit block, and wherein the second optical fiber waveguide provides for an aspect ratio transformation from a round input cross section to a linear output cross section that is compatible with the diode array spectrograph.

2. The coupler of claim 1 wherein the means for receiving an optical fiber waveguide comprises:

a fiber optic waveguide connector adapted to secure one end of the first optical fiber waveguide therein; and a sleeve coupled between the connector and the slit block that surrounds the second optical fiber waveguide.

3. The coupler of claim 2 which comprises a plurality of optical fiber waveguides coupled between the fiber optic waveguide connector and the slit block.

4. The coupler of claim 2 wherein the fiber optic waveguide connector comprises an SMA connector.

5. The coupler of claim 3 wherein the plurality of optical fiber waveguides comprises nine individual waveguides.

6. The coupler of claim 5 wherein the individual waveguides each comprise a 0.12 NA 50/55 $\mu$m silica fiber.

7. The coupler of claim 6 wherein the exit aperture has dimensions of approximately 50 $\mu$m $\times$ 500 $\mu$m.

8. A fiber optic coupler for use with a diode array spectrophotometer that comprises a diode array spectrograph including a holographic grating and a photodiode array, and a first optical fiber waveguide adapted to couple light from a sample under investigation to the spectrograph, said coupler comprising:

a optical fiber waveguide connector adapted to secure one end of the first optical fiber waveguide therein;

a slit block having a relatively thin, rectangular exit aperture that has predetermined dimensions compatible with the diode array spectrograph; and a second optical fiber waveguide coupled between the optical fiber waveguide connector and the slit block that has a generally round cross section adjacent the connector, and has a generally linear cross section adjacent the exit aperture of the slit block, and wherein the second optical fiber waveguide provides for an aspect ratio transformation from a round input cross section to a linear output cross section that is compatible with the diode array spectrograph.

9. The coupler of claim 8 wherein the second optical fiber waveguide comprises a plurality of optical fiber waveguides coupled between the optical fiber waveguide connector and the slit block.

10. The coupler of claim 8 wherein the fiber optic waveguide connector (26) comprises an SMA connector.

11. The coupler of claim 9 wherein the plurality of optical fiber waveguides comprises nine individual waveguides.

12. The coupler of claim 11 wherein the individual waveguides each comprise a 0.12 NA 50/55 $\mu$m silica fiber.

13. The coupler of claim 12 wherein the exit aperture has dimensions of approximately 50 $\mu$m × 500 $\mu$m.

14. A diode array spectrophotometer system comprising:
   a spectrograph including a holographic grating and a photodiode array detector;
   a light source;
   a first optical fiber waveguide adapted to couple light from the light source to a sample under investigation;
   a second optical fiber waveguide adapted to couple light from the sample under investigation (24) to the spectrograph; and
   a fiber optic coupler interposed between the second optical fiber waveguide and the spectrograph that comprises:
   means for receiving the second optical fiber waveguide;
   a slit block having a relatively thin, rectangular exit aperture that has dimensions compatible with the diode array spectrograph; and
   a third optical fiber waveguide coupled between the means for receiving the second optical fiber waveguide and the slit block adjacent the exit aperture thereof that has a generally round cross section adjacent the means for receiving the second optical fiber waveguide, and that has a generally linear cross section at an end adjacent the exit aperture of the slit block, and wherein the third optical fiber waveguide provides for an aspect ratio transformation from a round input cross section to a linear output cross section that is compatible with the diode array spectrograph.

15. The system of claim 14 wherein the means for receiving the second optical fiber waveguide comprises:
   a fiber optic waveguide connector adapted to secure one end of the second optical fiber waveguide therein; and
   a sleeve coupled between the connector and the slit block that is adapted to enclose the third optical fiber waveguide.

16. The system of claim 15 wherein the third optical fiber waveguide further comprises a plurality of optical fiber waveguides coupled between the fiber optic waveguide connector and the slit block.

17. The system of claim 16 wherein the plurality of fiber optic waveguides comprises nine individual waveguides.

18. The system of claim 17 wherein the individual waveguides each comprise a 0.12 NA 50/55 $\mu$m silica fiber, and the exit aperture has dimensions of approximately 50 $\mu$m × 500 $\mu$m.

19. The system of claim 14 further comprising:
   a plurality of collimating lenses adapted to collimate light from the first optical fiber waveguide, transmit the collimated light through the sample under investigation, and couple the light passing through the sample under investigation to the second optical fiber waveguide.

20. The system of claim 19 further comprising a focusing lens disposed between the light source and the first optical fiber waveguide adapted to focus light provided by the light source into the first optical fiber waveguide.

* * * * *